US009289273B2

(12) United States Patent
Staley

(10) Patent No.: US 9,289,273 B2
(45) Date of Patent: Mar. 22, 2016

(54) METHOD AND SYSTEM FOR BODILY TRANSLATING A TOOTH WITH A WIDE AND ADJUSTABLE WIDTH BRACKETS

(76) Inventor: Robert N. Staley, Iowa City, IA (US)

( * ) Notice: Subject to any disclaimer, the term of this patent is extended or adjusted under 35 U.S.C. 154(b) by 79 days.

(21) Appl. No.: 13/979,091

(22) PCT Filed: Jan. 11, 2012

(86) PCT No.: PCT/US2012/020877
§ 371 (c)(1),
(2), (4) Date: Jul. 10, 2013

(87) PCT Pub. No.: WO2012/097028
PCT Pub. Date: Jul. 19, 2012

(65) Prior Publication Data
US 2013/0323667 A1 Dec. 5, 2013

Related U.S. Application Data

(60) Provisional application No. 61/431,968, filed on Jan. 12, 2011, provisional application No. 61/452,839, filed on Mar. 15, 2011.

(51) Int. Cl.
A61C 7/14 (2006.01)
A61C 7/22 (2006.01)

(52) U.S. Cl.
CPC .... A61C 7/22 (2013.01); A61C 7/14 (2013.01)

(58) Field of Classification Search
CPC .............. A61C 7/12; A61C 7/14; A61C 7/20; A61C 7/22; A61C 7/28
USPC ........................... 433/8–16, 17–18
See application file for complete search history.

(56) References Cited

U.S. PATENT DOCUMENTS

| 4,256,455 | A | * | 3/1981 | Forster .............................. 433/8 |
| 4,917,602 | A | * | 4/1990 | Broussard ......................... 433/8 |
| RE34,044 | E | * | 8/1992 | Broussard ......................... 433/8 |
| 5,383,784 | A | * | 1/1995 | Sernetz ............................. 433/7 |
| 5,439,379 | A | * | 8/1995 | Hansen ............................. 433/8 |
| 5,879,156 | A | * | 3/1999 | DeLeo .............................. 433/9 |
| 5,954,502 | A | * | 9/1999 | Tuenge et al. ................... 433/16 |
| 6,017,216 | A | * | 1/2000 | DeLeo .............................. 433/9 |
| 6,554,612 | B2 | * | 4/2003 | Georgakis et al. .............. 433/11 |
| 7,175,428 | B2 | * | 2/2007 | Nicholson ....................... 433/11 |
| 7,306,458 | B1 | * | 12/2007 | Lu ................................... 433/16 |
| 7,431,586 | B1 | * | 10/2008 | Silverman ......................... 433/9 |
| 7,731,496 | B2 | * | 6/2010 | Minium .......................... 433/24 |
| 7,740,475 | B2 | * | 6/2010 | Minium .......................... 433/16 |
| 7,845,941 | B2 | * | 12/2010 | Minium .......................... 433/16 |
| 8,113,828 | B1 | * | 2/2012 | Greenfield ...................... 433/16 |
| 8,366,440 | B2 | * | 2/2013 | Bathen et al. ................... 433/16 |
| 8,371,846 | B2 | * | 2/2013 | Kishi .............................. 433/16 |
| 2007/0259302 | A1 | | 11/2007 | Jayawardena |
| 2008/0014544 | A1 | * | 1/2008 | Nucera ............................ 433/13 |
| 2009/0305183 | A1 | | 12/2009 | Chen |
| 2009/0325120 | A1 | | 12/2009 | Lewis |
| 2011/0269093 | A1 | * | 11/2011 | Waugh, Jr. ....................... 433/10 |
| 2012/0315593 | A1 | * | 12/2012 | Ramos-de-la-Pena et al. ... 433/9 |

FOREIGN PATENT DOCUMENTS

KR 100991835 11/2010

* cited by examiner

Primary Examiner — Cris L Rodriguez
Assistant Examiner — Hao D Mai
(74) Attorney, Agent, or Firm — Simmons Perrine Moyer Bergman PLC

(57) ABSTRACT

A system and method for translating teeth along an arch wire which utilizes brackets with larger dimensions and with variable dimensions so that larger lever arms are possible thereby reducing the need for excessive pressure and reducing occasions of excessive tooth rotation which is incidental to tooth translation.

23 Claims, 2 Drawing Sheets

METHOD AND SYSTEM FOR BODILY TRANSLATING A TOOTH WITH A WIDE AND ADJUSTABLE WIDTH BRACKETS

CLAIM OF PRIORITY

The present application is a national stage application under 35 U.S.C. 371 and/or a continuation under 35 U.S.C. §120 of PCT/US2012/020877, filed on Jan. 11, 2012, which claims the benefit of U.S. provisional application 61/452,839, filed on Mar. 15, 2011 and U.S. provisional application 61/431,968, filed on Jan. 12, 2011, all of which are incorporated by reference.

FIELD OF THE INVENTION

The present invention generally relates to orthodontic methods and appliances, and more particularly relates to the edgewise appliance, and even more particularly relates to methods and systems for bodily movement of teeth along an arch wire at times when excessive rotation of and or forces on a tooth would otherwise be a concern.

BACKGROUND OF THE INVENTION

Since 1928 and 1929 when Edward H. Angle first publicly described his invention of the edgewise appliance, the single width bracket he invented has been modified to correct tooth rotations in the horizontal plane. Since the 1990s the width of the brackets typically used by orthodontists have decreased over time. Two other dimensions of Angle's original rectangular edgewise slot, height of 22 mils and depth of 28 mils (one thousandths of an inch) are used by many orthodontists currently. A smaller 18 mil by 25 mil slot was invented and is used by a large number of orthodontists. In some cases, patient comfort and cosmetic appeal have motivated the decrease in width and size of these various components of the edgewise appliance.

While these smaller components have been used extensively in the past, they do have some drawbacks. First of all, while not wishing to be bound by theory, the applicant opines that when retracting upper canines in a typodont, using a nickel-titanium spring delivering initially 150 grams of force, the canine with a twin edgewise bracket (22 by 28 mil slot) and bracket width of 4.6 mm moved in a bodily manner along the 20 mil arch wire. In contrast, the canine with a twin edgewise bracket (22 by 28 mil slot) and bracket width of 2.2 mm experienced with the same spring force controlled tipping. Explanation: In the edgewise bracket the tooth is translated by a series of opposite rotations about the center of resistance (CR) in the root and about the center of the bracket. As a bracket is reduced in width and size, the lever arms within the bracket are also reduced in size which requires greater forces to operate them, hence the retraction force rotating the tooth about its CR overpowered the ability of the bracket and arch wire to create a couple to rotate the tooth about the center of the bracket. A wider bracket can more effectively translate a tooth along an arch wire than a narrower bracket. For both wide and narrow brackets, use of heavy forces probably increase the potential for undesirable consequences such as high amounts of root resorption. Narrow brackets are useful in the initial stages of tooth alignment because they have larger inter-bracket distances that allow flexible arch wires to properly align the teeth.

Consequently, there may exist a need for improved methods and systems for translating of teeth along an arch wire while minimizing rotation of teeth in an edgewise appliance.

SUMMARY OF THE INVENTION

It is an object of the present invention to provide a system and method for controlling rotation of a tooth in an edgewise appliance.

It is a feature of the present invention to utilize generally wider brackets.

It is an advantage of the present invention to create brackets which provide for longer lever arms for causing translation of the tooth along an arch wire.

It is another feature of the present invention to include larger slot depth and slot height dimensions of the brackets.

It is another advantage of the present invention to allow use of larger arch wires which also provide for longer lever arms for causing buccal-lingual rotation of the tooth.

It may be possible to reduce the magnitude of the rotations that occur in the translation and buccal-lingual movement of the teeth. The present invention may allow better operation of the physical properties in arch wires made of different alloys.

It is another object of the present invention to reduce the number of brackets that need to be placed on a given patient's teeth during the course of an extended treatment.

It is another feature of the present invention to use adjustable width brackets.

It is an advantage of the present invention to place one bracket on a tooth adjust it to a narrow bracket width to start and then later adjust the bracket width to be wider later on, all without removing the bracket from its position on a tooth.

Accordingly, the present invention is a system and method including a collection of larger and variable dimension brackets and a larger arch wire which are capable of having larger lever arms for rotating the tooth.

BRIEF DESCRIPTION OF THE DRAWINGS

The invention may be more fully understood by reading the following description of the preferred embodiments of the invention, in conjunction with the appended drawings wherein.

DETAILED DESCRIPTION

Figure 1:
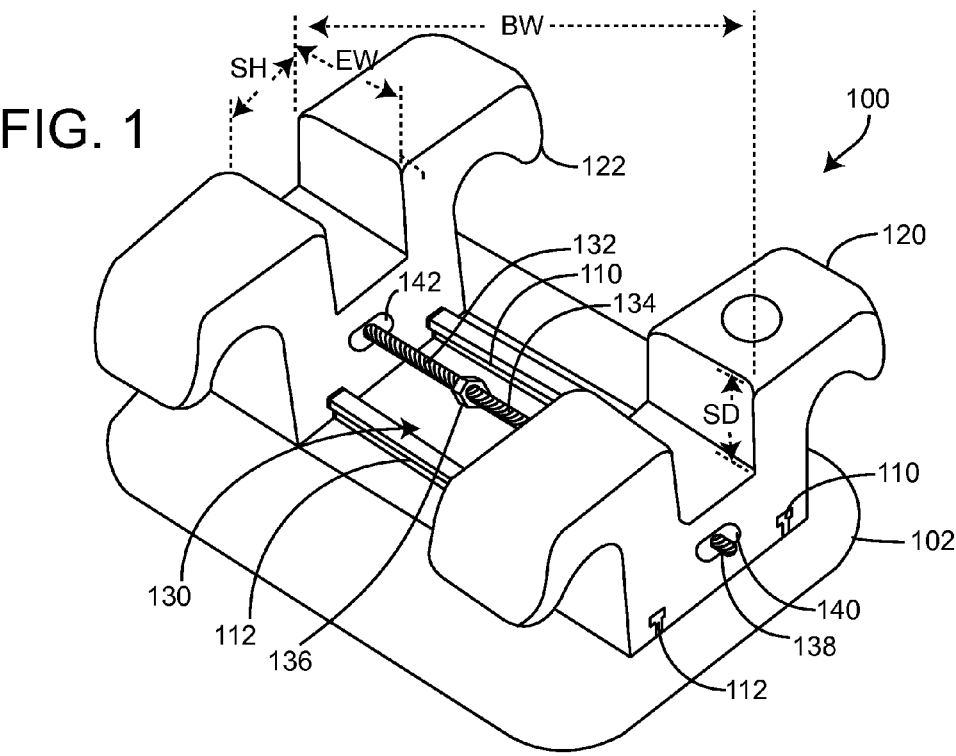
FIG. 1 is a perspective view of a bracket of the present invention, in an open or wide orientation.

Now referring to the drawings, wherein like numerals refer to like matter throughout, and more specifically referring to FIG. 1, there is shown an increased lever arm bracket of the present invention generally designated 100, which includes a bracket tooth mounting base 102 which could be made using materials, such as stainless steel, and methods which are well known in the art for making bases of other brackets. Bracket tooth mounting base 102 could have integrally formed therein or attached thereto a first base mounted guide rail 110 and a second base mounted guide rail 112 or other suitable support and translation permitting structure. Disposed upon said first base mounted guide rail 110 and second base mounted guide rail 112 in a movable and longitudinally translateable manner are first end ear structure 120 and second end ear structure 122 which are each structures which are very similar to corresponding portions of existing prior art twin brackets, except that they are detached from their base and are configured with longitudinal voids therein, which are configured to receive therein, the first base mounted guide rail 110 an second base mounted guide rail 112. The surfaces of first end ear structure 120 and second end ear structure 122, especially those surfaces which mate with first base mounted guide rail 110 and second base mounted guide rail 112 and those that touch bracket tooth mounting base 102, are preferable made to reduce and\or manage friction therebetween. First end ear structure 120 and second end ear structure 122 may have a longitudinal threaded channel extending from an exterior face to an interior face for receiving therein and operatively mating with a rotating linear adjusting spreading screw shaft 130 which extends between first end ear structure 120 and second end ear structure 122.

First end ear structure 120 and second end ear structure 122 are shown having two ears coupled to each other. The present invention is not limited to ear structures which have multiple ears per ear structure. The term ear is well known in the art and is used here to refer to that portion of the bracket which in combination with another adjacent ear forms a channel for the arch wire. Additionally, the ears are configured to receive thereon chains or other tooth to tooth connecting structures. Rotating linear adjusting spreading screw shaft 130 is configured with a male right handed threaded segment 132 and a male left handed threaded segment 134 which may mate with female at least partially threaded channels or in the alternative, the channels could be non-threaded and there could be a first threaded shaft receiving plate 140 and second threaded shaft receiving plate 142 coupled to first end ear structure 120 and second end ear structure 122 respectively. Rotating linear adjusting spreading screw shaft 130 and the threaded channels, plates or other structure at each end form a mechanism known as a separating screw or a turnbuckle, whereby rotation of the rotating linear adjusting spreading screw shaft 130 with its oppositely threaded male ends, mates with the female threaded structures and causes the first end ear structure 120 and second end ear structure 122 to either approach each other or separate depending upon the direction of rotation of rotating linear adjusting spreading screw shaft 130. To facilitate rotation of rotating linear adjusting spreading screw shaft 130 there is a central tool engaging region 136 which could be configured with various tool engaging structures such as a hole for receiving therein a pin or key or a hexagonal or other shaped section for mating with a wrench head, still other structures for facilitating rotation of the rotating linear adjusting spreading screw shaft 130 are envisioned. The ends of rotating linear adjusting spreading screw shaft 130 could be non-threaded hexagonal or similar shaped tips (not shown) which could be used to mate with a wrench.

Figure 2:
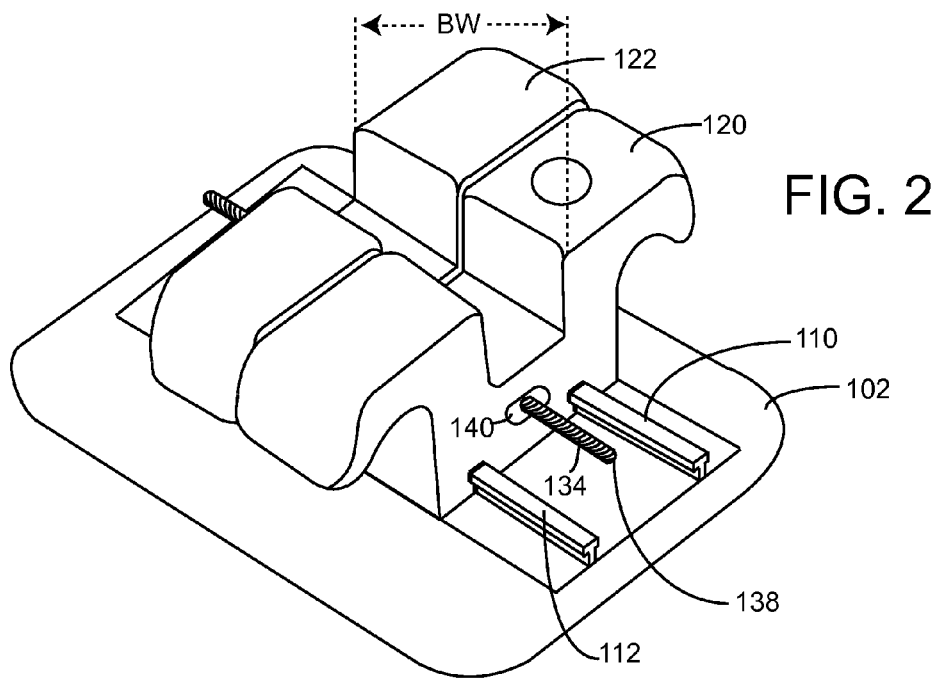
FIG. 2 is a perspective view of the bracket of FIG. 1 in a closed or narrow orientation.

FIG. 1 shows the increased lever arm bracket 100 in a fully extended or open position. When the rotating linear adjusting spreading screw shaft 130 is turned in a direction for closure, See FIG. 2, the left hand thread segment end 138 is shown protruding out of the first threaded shaft receiving plate 140, (without the optional hexagonal end) and the gap shown in FIG. 1, between first end ear structure 120 and second end ear structure 122 has been reduced. If it desired to completely close the bracket the optional hexagonal tips at the end of the shaft 130 could be used when access to the center of the shaft is difficult or impossible.

In many aspects the brackets of the present invention are similar in many ways to prior art stainless steel twin brackets, however, some key dimension are dramatically different from prior art brackets.

FIG. 1 shows the bracket width dimension BW which is preferably wider or capable of being adjusted to be wider than currently popular brackets. A preferred embodiment the present invention includes a system of brackets on various teeth to form an edgewise appliance where the maximum or open BW is approximately 70% to 80% of the tooth width. Ideally, the rotating linear adjusting spreading screw shaft 130 and cooperating elements of first end ear structure 120 and second end ear structure 122 can close enough so that the closed or minimum bracket width dimension BW is approximately 2-3 mm. The slot depth dimension SD is preferably substantially larger than current slot depths. Preferably the SD is 32 mils or between 32 and 39 mils, so a larger arch wire of stainless steel (SS), TMA or NiTi can be used and still provide the necessary forces to torque the tooth about its center of rotation. It should be understood that the current SD and arch wire sizes could be used in some embodiments of the present invention. Similarly, the ear width dimension EW is preferably 1 millimeter, but a range of 1 mm to 2 mm could be helpful. Of course the current and prior art EW could be used in some embodiments of the present invention. In a preferred embodiment the slot height dimension SH is 22 mils or within a range of 22 mils to 28 mils. Of course, current and prior art SH dimensions could be utilized in some embodiments of the present invention.

Figure 3:
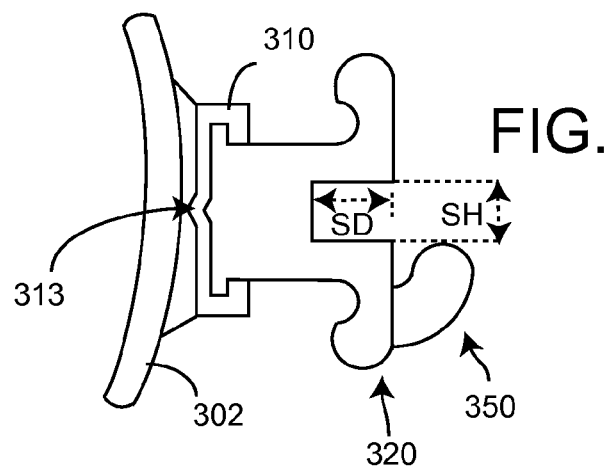
FIG. 3 is an end view of a bracket of the present invention.

Now referring to FIG. 3, there is shown an alternate embodiment of the present invention which utilizes discrete shims in a channel instead of the infinitely adjustable spreading screw and rail structures of FIG. 1. More particularly, there is shown a bracket with a guide channel 310 formed thereon or attached thereto. Disposed partially in guide channel 310 is first ear structure 320 which may be slid in from the end during assembly. Preferably an end cover (not shown) is attached to the end of guide channel 310 after insertion of first ear structure 320 so that first ear structure 320 cannot be accidentally separated from guide channel 310. Also shown is an optional hook 350.

First ear structure 320 is sized and configured to be translated within the guide channel 310. Bracket tooth mounting base 302, guide channel 310 and first ear structure 320 may be any suitable material but stainless steel may be preferred.

Figure 4:
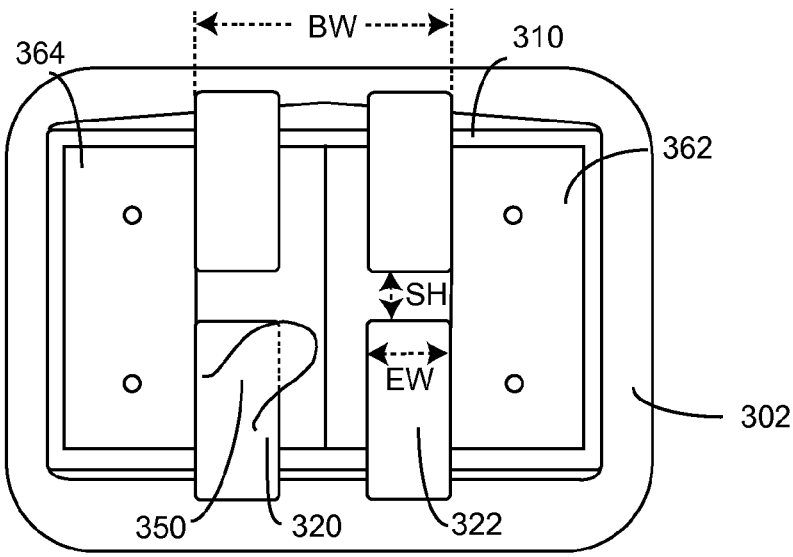
FIG. 4 is a top view of the bracket of FIG. 3 after being manipulated into a closed orientation.

To stop first ear structure 320 from moving around within the guide channel 310, second spacing shim 364 is used. Now referring to FIG. 4 there is shown a bracket of FIG. 3 where the first ear structure 320 has been moved to a central location in guide channel 310 for a closed bracket orientation, and second spacing shim 364 is shown disposed between the first ear structure 320 and the end of the guide channel 310. Also shown in FIG. 4 is second ear structure 322 and first spacing shim 362. This configuration of shims and ear structures results in a closed orientation of the adjustable bracket.

Figure 5:
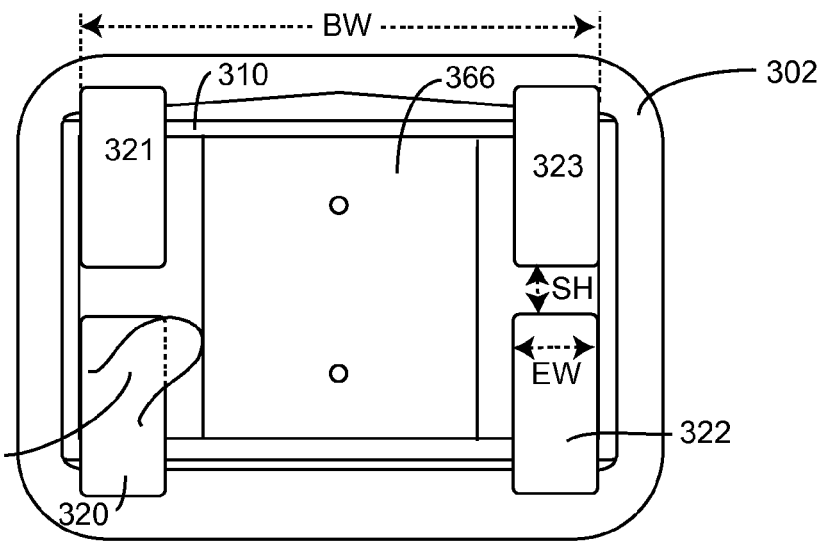
FIG. 5 is a top view of the bracket of FIG. 3 in an open orientation.

Now referring to FIG. 5, there is shown an open configuration of the adjustable bracket which includes the first ear structure 320 and the second ear structure 322 separated by a third spacing shim 366. Note that the spacing shims are preferably made of some resilient non-toxic material with sufficient resilience to allow them to be bent slightly so they can be inserted into and removed from the guide channel 310 from the top and yet provide for minimal compression in a direction parallel with the guide channel 310 so as to hold the first ear structure 320 and second ear structure 322 in a stable arrangement. It should be understood that intermediate separations and even non-centralized locations of first ear structure 320 and second ear structure 322 could be accomplished by using other sized shims or placement of the shims. For example, a configuration of an adjustable bracket could be deployed where first spacing shim 362 of FIG. 4 is moved from its location shown in FIG. 4 to a position between first ear structure 320 and second ear structure 322. Many different sizes and combinations of shims could be provided to an orthodontist as kit for adjusting the width of the bracket. The shims could be coded so that the separation between the first ear structure 320 and structure 322 can be ascertained by reviewing these codes on the shims and their placement within the guide channel 310 and no measurements would be necessary.

In operation, the present invention comprises a method of moving teeth in a human mouth which utilized many known orthodontic methods and practices. Preferably, the method of the present invention provides for use of just one twin bracket attached to each tooth during the duration of the orthodontic treatment, which could take several months. For example, it may be preferred that the increased lever arm bracket 100 be deployed in a closed position at the beginning of treatment and as the treatment progresses the width of the various increased lever arm brackets 100 are opened up or made wider. In the alternative, if a version of the increased lever arm bracket 100 is used which is not adjustable, it is desired that the wider range of bracket dimensions mentioned above be used. It is understood that arch wire changes may be made at various points in the treatment.

Throughout this description, reference is made to stainless steel central male components and distal female components because it is believed that the beneficial aspects of the present invention would be most readily apparent when used in connection with such configurations, however, it should be understood that the present invention is not intended to be limited to such matter and should be hereby construed to include any suitable mating configuration and material including TMA, NiTi, ceramics, plastics, etc. Throughout this description TMA is used herein to refer to the titanium, molybdenum, zirconium, and tin alloy commonly referred to in the industry as TMA.

Throughout this description, reference is made to a "separating screw" this term is herein defined to mean a device which changes amount of separation of structures coupled to it depending up the rotation of a central threaded shaft with opposite threads at each end, which are coupled to female threaded members, which are coupled to objects which will not rotate but are free to translate when the central threaded shaft is rotated. This rotation of the central threaded shaft will thereby cause the female threaded members to either approach each other or separate; i.e., adjust their separation, depending upon the direction of rotation of the central threaded shaft. The term "turnbuckle" is defined herein to mean a device which is similar to the spreading screw except that the central member that is rotated is a not a threaded shaft with opposing threads on male ends, but a pair of separated female threaded members which are fixed with respect to each other and are configured to receive therein threaded male shafts. When the central female members are rotated as a unit the male members are either brought closer to one another or separated, depending upon the direction of rotation of the central female members.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

I claim:

1. An adjustable width twin-edgewise appliance system comprising:
   a twin-edgewise bracket configured to be attached to a first tooth having a first tooth width, where said twin-edgewise bracket has an adjustable bracket width dimension BW and comprises:
   a first base member, configured to be bonded to said first tooth;
   a first two ear edgewise bracket coupled to said first base member;
   a second two ear edgewise bracket coupled to said first base member;
   while said base member is coupled to said first tooth, one of said first two ear edgewise bracket and said second two ear edgewise bracket being translatable with respect to said first base member and with respect to another of said first two ear edgewise bracket and said second two ear edgewise bracket, so as to vary a variable minimum separation distance, VSD, between said first two ear edgewise bracket and said second two ear edgewise bracket;
   each of said first two ear edgewise bracket and said second two ear edgewise bracket having two ears fixed with respect to each other which define an arch wire slot having:
   a predetermined and fixed slot depth dimension SD;
   a predetermined and fixed slot height dimension SH, which is defined by a minimum separation distance between said two ears;
   a predetermined and fixed ear width dimension EW; and
   an arch wire running across said first two ear edgewise bracket and to and across said second two ear edgewise bracket in an arch wire longitudinal direction, which is parallel with said BW and said EW and where said BW=said EW+said VSD+said EW.

2. The system of claim 1 wherein said SH is substantially 22 mils and where said EW is within a range of 1 mm to 2 mm.

3. The system of claim 2, wherein said EW is substantially 1 mm and said BW is within the range of 70% to 80% of said first tooth width.

4. A method of moving teeth in a mouth comprising the steps of:
   attaching a plurality of twin-edgewise brackets each to a different one of a plurality of teeth, where each of said plurality of twin-edgewise brackets has
   an adjustable bracket width dimension BW and comprises:
   a plurality of two ear structures which are translatably variably spaced with respect to each other, and each of said plurality of two ear structures comprising:
   a plurality of ears which are fixed with respect to each other and are separated by
   a predetermined and fixed slot height dimension SH;
   each of said plurality of ears having a fixed ear width dimension EW;
   providing an arch wire; and
   placing said arch wire through and between a plurality of two ear structures on a first one of said plurality of twin-edgewise brackets;
   adjusting the BW of said first one of said plurality of twin-edgewise brackets, by translating one of said plurality of two ear structures while said first one of said plurality of twin-edgewise brackets is attached to one of said plurality of teeth.

5. The method of claim 4 wherein said EW is within the range of 1 mm to 2 mm and the method further comprising the steps of:

adjusting the BW of each of said plurality of twin-edgewise brackets.

6. The method of claim 5 wherein said step of adjusting said BW comprises the step of moving an ear of one of said plurality of brackets and moving a first spacing shim to change said BW.

7. A method of moving teeth in a mouth comprising the steps of:
providing a plurality of brackets each being configured to be attached to a different one of a plurality of teeth, where each bracket has:
a bracket width dimension BW within a range of 70% to 80% of a tooth width;
a slot depth dimension SD with a range of 32 mils to 39 mils;
a slot height dimension SH within a range of 22 mils to 28 mils;
an ear width dimension EW within a range of 1 mm to 2 mm;
providing an arch wire;
placing said arch wire through each of said plurality of brackets; and
adjusting the BW of each of said plurality of brackets;
wherein said step of adjusting said BW comprises the step of rotating a rotating linear adjusting spreading screw shaft.

8. An adjustable width twin-edgewise appliance comprising:
an arch wire, having an arch wire longitudinal direction, configured and shaped to guide movement of teeth in a mouth; and
an adjustable width twin-edgewise bracket, having a bracket width BW, comprising:
a base configured to be coupled to a tooth;
a first ear structure, translatably coupled to said base and configured with two first ears which are fixed with respect to each other and each having an ear width EW and having a first slot therebetween and with a predetermined and dimensionally fixed slot height SH which is the separation between said two first ears and a slot depth SD therein, which first slot is configured to receive said arch wire therein in a first arch wire orientation, and a second ear structure, translatably coupled to said base which is configured with two second ears which are fixed with respect to each other and having a second slot therebetween and with a predetermined and dimensionally fixed slot depth SD and slot height SH which is the separation between said two second ears therein to receive said arch wire in a second arch wire orientation, where said first ear structure and said second ear structure are configured, while said base is coupled to said tooth, to be translatable, with respect to each other and along the arch wire longitudinal direction, to a variable separation distance VSD therebetween without changing either of said first arch wire orientation, which is parallel with said EW, and said second arch wire orientation, which is parallel with said EW, and said adjustable width bracket being coupled to said arch wire and capable of being moved in either a mesial or distal direction along said arch wire, where said BW=said EW+said VSD+said EW.

9. The edgewise appliance of claim 8 wherein said first ear structure is restrained from movement in at least one direction by a first spacing shim.

10. An edgewise appliance comprising:
an arch wire configured and shaped to guide movement of teeth in a mouth;

an adjustable width bracket, having a bracket width BW, coupled to said arch wire and capable of being moved along said arch wire;
a means for adjusting said BW of the adjustable bracket, wherein said means for adjusting comprises:
a first base mounted guide rail;
a first end ear structure; translatably disposed on said first base mounted guide rail;
a second end ear structure; translatably disposed on said first base mounted guide rail; and
a rotating linear adjusting spreading screw shaft extending between said first end ear structure and said second end ear structure.

11. The edgewise-appliance of claim 10 wherein said rotating linear adjusting spreading screw shaft comprises a right handed threaded segment and a left handed threaded segment with a central tool engaging region disposed therebetween.

12. An edgewise appliance comprising:
an arch wire configured and shaped to guide movement of teeth in a mouth; and
an adjustable width bracket coupled to said arch wire and capable of being moved along said arch wire;
wherein adjustable bracket comprises a movable ear configured to be translated along a bracket tooth mounting base so as to change a bracket width BW of said adjustable bracket; and
wherein said movable ear is moved by a spreading screw with a central tool engaging region which comprises hexagonal section configured to mate with a wrench.

13. An adjustable width twin-edgewise bracket for use with an arch wire, the adjustable width twin-edgewise bracket comprising:
a base, configured to be adhesively coupled to a front surface of a tooth;
a first ear structure coupled to said base;
said first ear structure having therein a first arch wire receiving slot having a fixed first slot depth, a fixed first slot height, and a fixed first arch wire internal orientation with respect to said first ear structure;
a second ear structure moveably coupled to said base;
said second ear structure having therein a second arch wire receiving slot having a fixed second slot depth, a fixed second slot height, and a fixed second arch wire internal orientation with respect to said second ear structure; and
so that a separation distance between said first ear structure and said second ear structure can be adjusted without removing said base from a tooth after said base has been affixed to the tooth and without changing a co-linear relationship between said first arch wire internal orientation and said second arch wire internal orientation.

14. The bracket of claim 13 wherein said first ear structure is movably coupled to said base.

15. The bracket of claim 14 wherein said first ear structure and said second ear structure are each translatably movable by use of a means for mating said first ear structure and said second ear structure to said base.

16. The bracket of claim 15 further comprising a resilient means for maintaining the separation between said first ear and said second ear.

17. The bracket of claim 13 further comprising an actuator configured to move said second ear structure with respect to said first ear structure.

18. An adjustable width bracket for use with an arch wire, the bracket comprising:
a base, configured to be adhesively coupled to a front surface of a tooth;
a first ear coupled to said base;

a second ear moveably coupled to said base, so that a separation distance between said first ear and said second ear can be adjusted without removing said base from a tooth after said base has been affixed to the tooth;

an actuator configured to move said second ear with respect to said first ear; and wherein said first ear is movably coupled to said base; and said actuator is configured to move both said first ear and said second ear.

19. An adjustable width bracket for use with an arch wire, the bracket comprising:
   a base, configured to be adhesively coupled to a front surface of a tooth;
   a first ear coupled to said base;
   a second ear moveably coupled to said base, so that a separation distance between said first ear and said second ear can be adjusted without removing said base from a tooth after said base has been affixed to the tooth;
   wherein said first ear and said second ear are each translatably movable by use of a means for mating said first ear and said second ear to said base; and
   a spreading screw configured to control the separation between the first ear and the second ear and where the means for mating is a pair of rails.

20. An adjustable width twin-edgewise bracket for use with an arch wire in an edgewise appliance, the adjustable width twin-edgewise bracket, having a bracket width and comprising:
   a bracket tooth mounting base, configured to be coupled to a first tooth;
   a first end ear structure having a first arch wire receiving slot which has a fixed slot height SD which is defined by a separation distance between a first plurality of ears which are fixed with respect to each other and a second end ear structure having a second arch wire receiving slot which has said fixed slot height SD which is defined by a separation distance between which defined by a second plurality of ears which are fixed with respect to each other and said second arch wire receiving slot which is co-linear with respect to said first arch wire receiving slot;
   means for coupling and translating at least one of said first end ear structure and said second end ear structure on said bracket tooth mounting base, which is coupled to said tooth, so as to change a variable minimum separation distance between said first end ear structure and said second end ear structure while maintaining a co-linear relationship between said first arch wire receiving slot and said second arch wire receiving slot.

21. The adjustable bracket of claim 20 wherein the means for coupling comprises a guide channel.

22. The adjustable bracket of claim 20 wherein in the means for coupling comprises a rail.

23. An adjustable bracket for use with an arch wire in an edgewise appliance, the adjustable bracket comprising:
   a bracket tooth mounting base;
   a first end ear structure and a second end ear structure;
   means for coupling said first end ear structure and said second end ear structure to so as to provide for an adjustable location on the bracket tooth mounting base for at least one of the first end ear structure and the second end ear structure; and
   a resilient removable spacer disposed between the first end ear structure and the second end ear structure and configured to be removed inserted and/or removed without a need to detach either of the first end ear structure or the second end ear structure from the bracket tooth mounting base.

\* \* \* \* \*